US011289204B2

(12) United States Patent
Brown et al.

(10) Patent No.: US 11,289,204 B2
(45) Date of Patent: Mar. 29, 2022

(54) AUTOMATIC DETERMINATION OF UNDERLYING REASONS FOR PATIENT FAILURES TO ADHERE TO PATIENT CARE PLANS

(71) Applicant: INTERNATIONAL BUSINESS MACHINES CORPORATION, Armonk, NY (US)

(72) Inventors: Eric W. Brown, New Fairfield, CT (US); Maria Eleftheriou, Mount Kisco, NY (US); Anca Sailer, Scarsdale, NY (US); Ching-Huei Tsou, Briarcliff Manor, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 220 days.

(21) Appl. No.: 15/840,568

(22) Filed: Dec. 13, 2017

(65) Prior Publication Data

US 2019/0180876 A1 Jun. 13, 2019

(51) Int. Cl.
| | | |
|---|---|---|
| *G16H 50/30* | (2018.01) | |
| *G16H 20/10* | (2018.01) | |
| *G16H 10/60* | (2018.01) | |
| *G16H 20/30* | (2018.01) | |
| *G16H 40/63* | (2018.01) | |
| *G16H 40/67* | (2018.01) | |

(52) U.S. Cl.
CPC ............ *G16H 50/30* (2018.01); *G16H 10/60* (2018.01); *G16H 20/10* (2018.01); *G16H 20/30* (2018.01); *G16H 40/63* (2018.01); *G16H 40/67* (2018.01)

(58) Field of Classification Search
CPC ......... G16H 50/30; G16H 10/60; G16H 20/10
USPC ............................................................. 705/2
See application file for complete search history.

(56) References Cited

U.S. PATENT DOCUMENTS

| | | | | |
|---|---|---|---|---|
| 6,850,252 | B1 * | 2/2005 | Hoffberg | G06K 9/00369 348/E7.061 |
| 8,126,735 | B2 * | 2/2012 | Dicks | G06Q 10/10 705/2 |
| 2003/0225597 | A1 * | 12/2003 | Levine | G16H 50/20 705/3 |
| 2005/0197545 | A1 * | 9/2005 | Hoggle | G06F 19/325 600/300 |
| 2007/0177779 | A1 * | 8/2007 | Dennison | G06K 9/42 382/128 |

(Continued)

OTHER PUBLICATIONS

Kohn, M. S., et al., "IBM's Health Analytics and Clinical Decision Support," Yearbook of Medical Informatics 9, No. 1, 2014, pp. 154-162.

*Primary Examiner* — Michael Tomaszewski
*Assistant Examiner* — Rachael Sojin Stone
(74) *Attorney, Agent, or Firm* — Erik A. Huestis; Stephen J. Kenny; Foley Hoag, LLP

(57) ABSTRACT

Automatic determination of underlying reasons for lack of treatment adherence is provided. In various embodiments, patient information for a patient is retrieved. The patient information comprises a treatment plan. A failure of compliance with the treatment plan by the patient is determined from the patient information. The failure of compliance and the patient information are evaluated to determine one or more potential cause of the failure of compliance. The one or more potential cause is provided to a user for review.

17 Claims, 4 Drawing Sheets

(56) References Cited

U.S. PATENT DOCUMENTS

| | | | |
|---|---|---|---|
| 2011/0245283 A1* | 10/2011 | Murata | A61K 31/366 514/275 |
| 2012/0266251 A1* | 10/2012 | Birtwhistle | H04W 12/003 726/26 |
| 2013/0035951 A1* | 2/2013 | Frey | G16H 50/30 705/2 |
| 2015/0112703 A1* | 4/2015 | Sysko | G16H 10/60 705/2 |
| 2015/0324527 A1* | 11/2015 | Siegel | G16H 10/60 705/3 |
| 2016/0140300 A1* | 5/2016 | Purdie | G06F 19/3481 705/2 |
| 2016/0171525 A1* | 6/2016 | Ezra | G06Q 30/0225 705/14.12 |
| 2016/0224762 A1 | 8/2016 | Gibson et al. | |
| 2017/0076059 A1 | 3/2017 | Morefield | |
| 2017/0132371 A1 | 5/2017 | Amarasingham et al. | |
| 2017/0329917 A1* | 11/2017 | McRaith | G16H 10/20 |
| 2020/0219262 A1* | 7/2020 | Hsiao | G06N 3/0454 |
| 2020/0261412 A1* | 8/2020 | Liu | A61K 38/1709 |
| 2020/0405134 A1* | 12/2020 | Hameed | G16H 40/63 |
| 2021/0319887 A1* | 10/2021 | Derrick, Jr. | G16H 80/00 |
| 2021/0383918 A1* | 12/2021 | Martin | G16H 40/67 |

\* cited by examiner

AUTOMATIC DETERMINATION OF UNDERLYING REASONS FOR PATIENT FAILURES TO ADHERE TO PATIENT CARE PLANS

BACKGROUND

Embodiments of the present disclosure relate to improved patient care, and more specifically, to determination of underlying reasons for patient failures to adhere to patient care plans.

BRIEF SUMMARY

According to embodiments of the present disclosure, methods of and computer program products for determining underlying reasons for lack of treatment adherence are provided. In various embodiments, patient information for a patient is retrieved. The patient information comprises a treatment plan. A failure of compliance with the treatment plan by the patient is determined from the patient information. The failure of compliance and the patient information are evaluated to determine one or more potential cause of the failure of compliance. The one or more potential cause is provided to a user for review.

DETAILED DESCRIPTION

Tracking patient compliance with a care plan is an important aspect of medical treatment. Various computer systems may be used to determine whether a patient is adhering to their patient care plan. Data may be extracted from monitoring systems and compared to a corresponding metric requirement to determine if the patient is adhering to their goal. For example, an exercise plan may be monitored by tracking steps walked each day or weight, which may be compared to target values. However, a tracking approach is limited to structured information and does not provide insight as to the underlying reasons why a patient may not be adhering to their patient care plan.

Accordingly, the present disclosure provides for analysis of patient information gathered from a variety of sources to determine underlying reasons why a patient may not be adhering to their patient care plan. These underlying reasons may not be identifiable from structured information alone. In various embodiments, natural language processing is applied to clinical notes and other sources. In various embodiments, correlations are detected between information from these various sources in order to identify underlying reasons as to a failure to adhere to a patient care plan.

Figure 1:
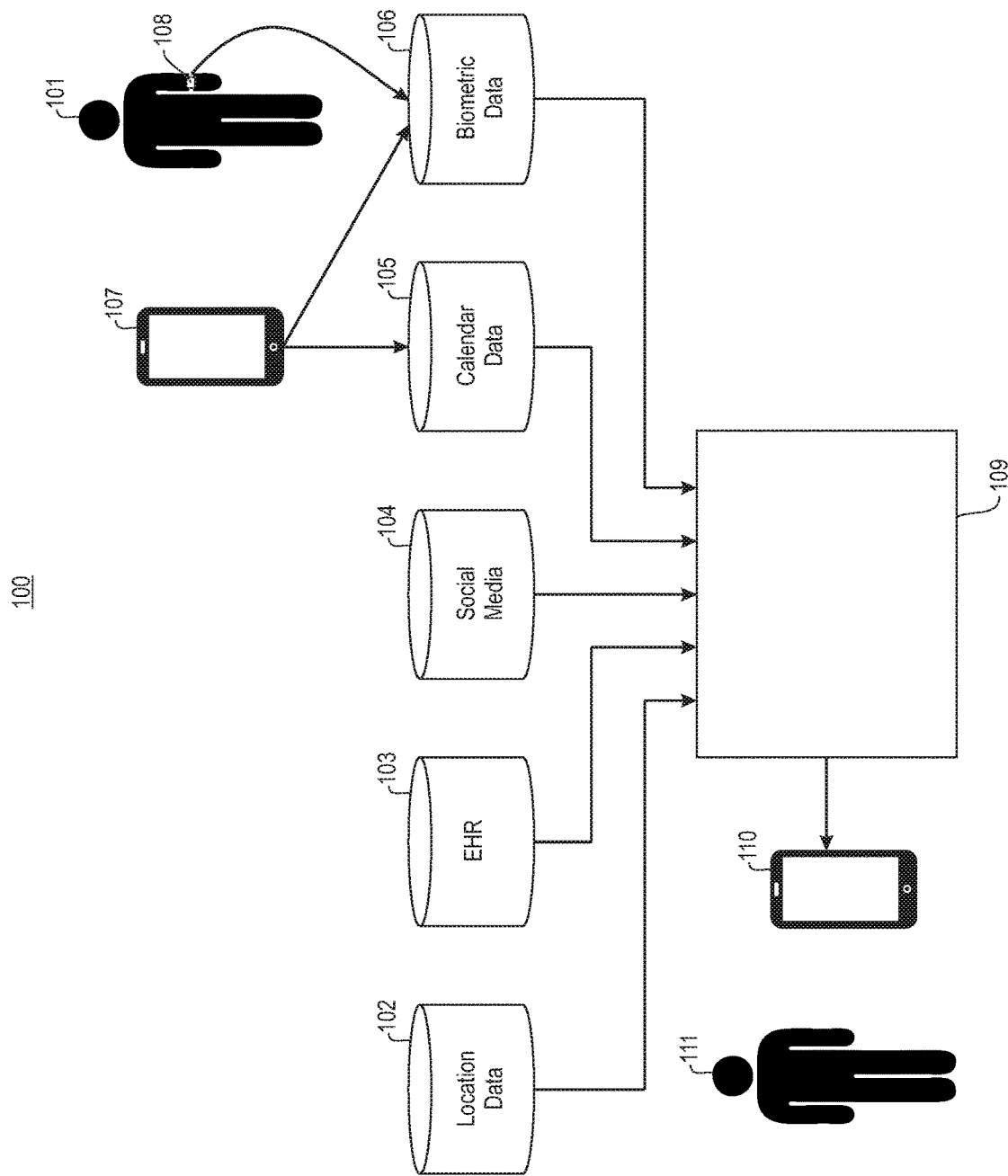
FIG. 1 illustrates a system for determination of underlying reasons for patient failures to adhere to patient care plans.

With reference now to FIG. 1, a system for determination of underlying reasons for patient failures to adhere to patient care plans is illustrated according to embodiments of the present disclosure. Structured and unstructured data about a patient 101 is obtained from a plurality of different sources 102 . . . 106. Data sources may include location data 102 electronic health records 103, social media data 104, calendar data 105, biometric data 106, or other sources of data regarding a patients behavior and activities, or about the patient's care plan. The care plan may relate to pharmaceutical dosage, medical treatment, exercise, or any other scheduled activity.

In various embodiments, calendar data 105 may be drawn from a mobile device 107 of patient 101, or other computing device. In various embodiments. Biometric data 106 may be drawn from mobile device 107 or wearable device 108 of patient 101, or another computing device or sensor.

Social media data 104 may include textual entries provide by patient 101 or related to patient 101. Social media data 104 may also include images of patient 101, or related to the location or environment of patient 101. Social media data 104 may also include relationship information for patient 101, including family membership, friendship, or professional relationships.

Electronic health record data 103 may include various medical data related to patient 101. In general, an electronic health record (EHR), or electronic medical record (EMR), may refer to the systematized collection of patient and population electronically-stored health information in a digital format. These records can be shared across different health care settings. Records may be shared through network-connected, enterprise-wide information systems or other information networks and exchanges. EHRs may include a range of data, including demographics, medical history, medication and allergies, immunization status, laboratory test results, radiology images, vital signs, personal statistics like age and weight, and billing information. EHR systems may be designed to store data and capture the state of a patient across time. In this way, the need to track down a patient's previous paper medical records is eliminated. In addition, an EHR system may assist in ensuring that data is accurate and legible. It may reduce risk of data replication as the data is centralized. Due to the digital information being searchable, EMRs may be more effective when extracting medical data for the examination of possible trends and long term changes in a patient. Population-based studies of medical records may also be facilitated by the widespread adoption of EHRs and EMRs.

Location data 102 may include information regarding the location of patient 101, for example based on tracking through mobile device 107. Location data 102 may include geocoded information, for example providing an address or location of interest for the location of patient 101. In some embodiments, location data may be tagged with additional information relative to patient 101, for example associating a given address with home, work, or school.

Data from sources 102 . . . 106, as well as any additional data sources are aggregated by server system 109. As outlined above, in some embodiments, structured data are available regarding the overall condition of the patient, patient schedule, and treatment plan. In some embodiments, additional unstructured data are available. For example, textual notes may be included in electronic health records or in social media posts. Textual data may be analyzed to determine patient activities, patient care plan, course of treatment, goals of treatment, or other information regarding patient 101.

It will be appreciated that a variety of natural language processing techniques may be applied to unstructured textual data. For example, keywords may be extracted that are indicative of compliance or non-compliance with a treatment plan, that are indicative of events of interest (e.g., meals, beverages, travel), or that indicate difficulty in compliance. More generally, known algorithms for topic identification may be used to determine location topics of note within unstructured data, known algorithms for named entity recognition may be used to identify entities of note, or known sentiment analysis algorithms may be used to identify a patient sentiment. Likewise, sentiment analysis of messages sent to and from a patent (e.g., via social media) may be performed to determine the type of relationship a given patient has with others (e.g., friendly, adversarial, etc.). In various embodiments, IBM Watson is used for natural language processing.

In some embodiments, structured data are used to understand the overall condition of the patient while the unstructured data are processed to identify the patient care plan, course of treatment, or the ultimate goals that are sought by the patient care plan or course of treatment. However, it will be appreciated that various structured and unstructured data sources may be used as set out herein.

Figure 2:
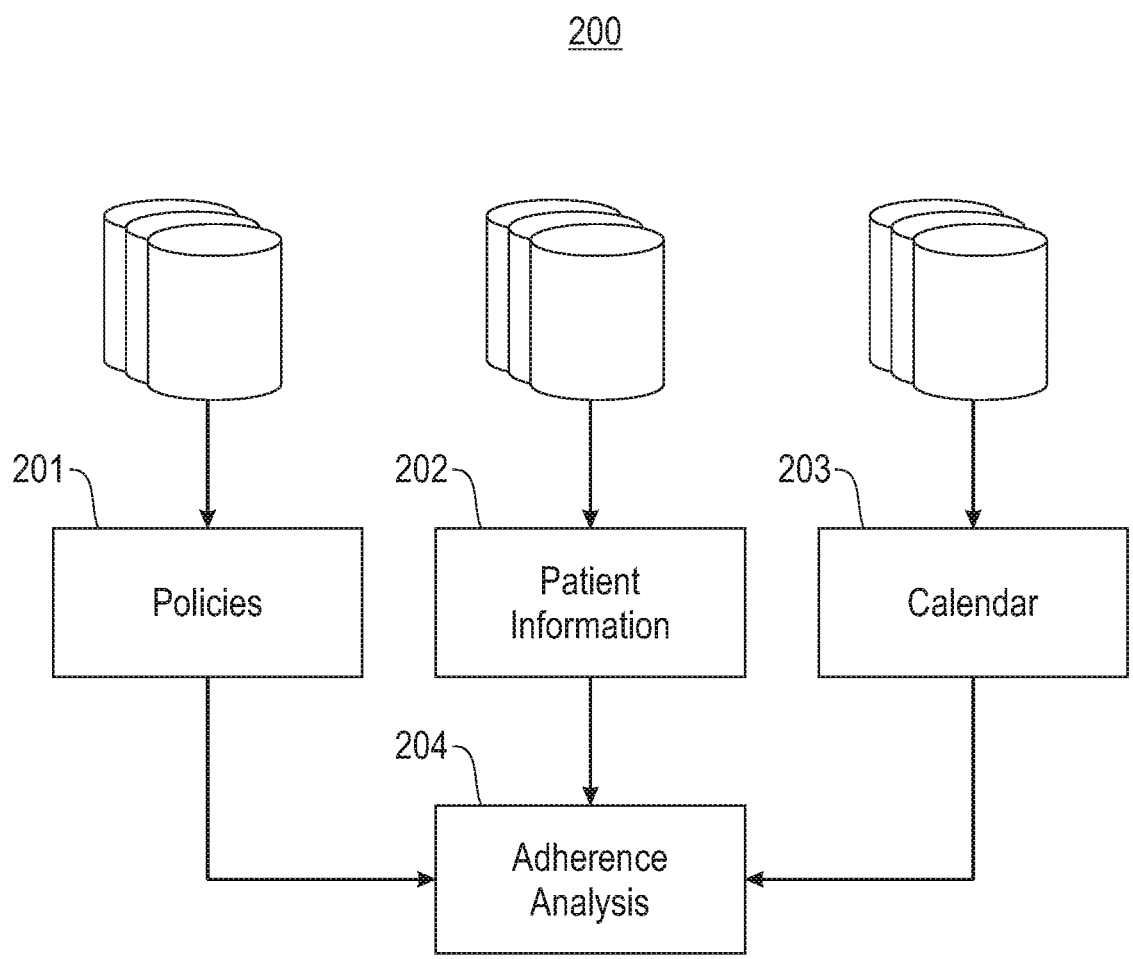
FIG. 2 is a flow diagram for patient adherence analysis according to embodiments of the present disclosure.

Referring now to FIG. 2, a flow diagram for patient adherence analysis is provided according to embodiments of the present disclosure. Policies 201 may include prescription guidelines, such as time, dosage frequency, restrictions on alcohol, or other requirements for compliance with a treatment plan. Likewise, policies 201 may include various target values for. Patient information 202 may include medical records information, such as vitals, current prescriptions, responsiveness, or allergies. Patient information 202 may also include additional patient information such as other people living with the patient or other relationships of the patient. Patient information 202 may also include environmental or other information related to the patient, such as temperature or weather. Calendar 203 may include schedules, events, meetings, travel, sleep times, and characteristics thereof.

Each of policies 201, patient information 202, and calendar 203 may be collected from structured or unstructured data as set forth above. These data provide the basis for identifying areas where the patient may not be adhering to their patient care plan. For example, statements indicative of a failure to adhere to the patient care plan may be collected as set forth above. Similarly, patient information may be compared to target values to determine compliance. For example, logged treatment events may be compared to the target treatment frequency.

Having identified areas where a patient is failing to adhere to the patient care plan or achieve the desired goals further adherence analysis 204 is performed to determine possible reasons for the failure to adhere to the patient care plan. The reasons may be tied to the particular portion of the patient care plan that is not being adhered to, or a goal that is not being achieved. The system may first categorize the failure and then explore reasons tied to that particular category of failure.

In some embodiments, potential reasons for an adherence failure may be learned. For example, over a plurality of users, association rule learning may be applied to learn associations between causes and adherence failures. It will be appreciated that a variety of machine learning techniques are available for such rule-based machine learning, such as learning classifier systems. In some embodiments, potential reasons for compliance failures are expert generated. In some embodiments, these expert-generated associations take the form of rules. For example, expert determined rules may define associations like (appointment before 9 am→failure to appear).

The analysis of a given type of failure may involve cross-correlating information from a variety of sources including, e.g., the patient EMR, pharmacy information, retail establishment computer systems, or hospital systems, to generate a plurality of hypotheses for the failure.

For example, a patient with hypertension may be prescribed a suitable medication. The patient may supply basic information in an electronic questionnaire, whether as part of a visit to a doctor or online. The questionnaire may include various baseline information about the patient and their attributes. The patient may expressly indicate on the questionnaire that they have not been taking their medication, or a determination that they have failed to take their medication may be made based on other patient data, such as social media. For example, the patient's electronic medical records and related pharmacy information may be automatically analyzed to determine that the patient has not picked up their medication and so is likely not in compliance with the dosage regiment. Given that the patient has not been taking their medication, systems according to the present disclosure look for reasons as to why the patient is not taking their medication.

In various embodiments, a ranked listing of possible reasons for the failure may be generated. As noted above, non-medical sources of information may also be used to gather insights into the lifestyle of the patient.

Once potential reasons have been generated by adherence analysis 204, the reasons may be displayed to a physician for further action. For example, server 109 may provide the reasons to mobile device 110 of doctor 111 for reference during an in-office visit. In some embodiments, the reasons may be ranked for display to the doctor. For example, the reasons may be ranked based on frequency in the general population, or within a particular population of interest. In addition, potential responsible relationships may be detected, e.g., by analyzing express relationships from social media or by sentiment analysis of messages. Potential responsible relationships may be provided to the doctor as potential avenues for treatment supervision and support for the patient.

In this way, treatment of the patient is improved by determining why the patient is not taking their medication, rather than merely that they are not taking it. As noted above. The hypothetical reasons generated based on patient data may be drawn from a set of predetermined failures, or may be learned over time. For example, a set of predefined hypotheses for a failure to take medication may include: too expensive, negative side effects, inconvenient to obtain medication, conflicts with other medications, or forgetfulness. Evidence for each of these hypotheses may be gathered from analysis of the patient EMRs and other information sources to determine the most probable reason and a potential solution. For example, it may be determined that the patient lives at least 10 miles away from the nearest pharmacy. This information may be gathered, e.g., from home address information in a patient's EMR, pharmacy information, and geographical information from a mapping system. Applying a predetermined or learned rule, this is evidence that picking up medication is inconvenient for the patient. The physician may suggest a mail order service as part of ensuring adherence to the medication care plan, and thus helping obtain a batter patient outcome.

In another example, results of a pharmaceutical treatment may be assessed instead of patient compliance alone. Where a patient is not meeting treatment goals, e.g., by not reaching a target blood pressure, but is in compliance with dosage regimen, an alternative explanation may be sought. Efficacy of a given pharmaceutical may be affected by interaction with foods or other pharmaceuticals. Accordingly, based on a predetermined or learned rule associating dosage time and meal time, a potential reason for failure to meet a treatment goal may be suggested.

In another example, a patient calendar may be leveraged to help identify delays in purchasing a pharmaceutical. Such a potential failure of compliance may be identified proactively, and the physician or patient may be notified in advance of scheduled travel.

In another example, vomiting may be offered as a potential reason for non-compliance where it is a side effect of a given pharmaceutical. A doctor may then check in with the patient regarding occurrence of the side effect, and take it into account when formulating future care plans.

Figure 3:
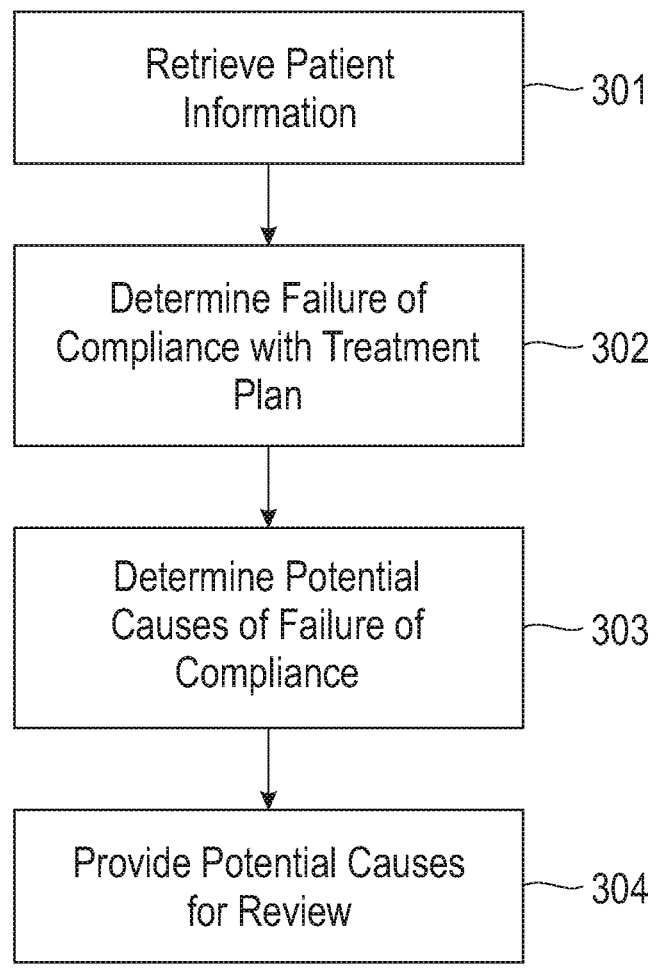
FIG. 3 illustrates a method of determining underlying reasons for lack of treatment adherence according to embodiments of the present disclosure.

With reference now to FIG. 3, a method of determining underlying reasons for lack of treatment adherence is illustrated according to embodiments of the present disclosure. At 301, patient information for a patient is retrieved. The patient information comprises a treatment plan. At 302, a failure of compliance with the treatment plan by the patient is determined from the patient information. At 303, the failure of compliance and the patient information are evaluated to determine one or more potential cause of the failure of compliance. At 304, the one or more potential cause is provided to a user for review.

In various embodiments, the patient information further comprises an electronic health record, biometric data, location data, calendar data, or social media data. In various embodiments, the patient information comprises structured and unstructured data.

In various embodiments, the treatment plan comprises a pharmaceutical dosage regimen. In various embodiments, determining the failure of compliance comprises comparing one or more treatment event of the patient information with the treatment plan.

In various embodiments, determining the one or more potential cause comprises comparing one or more predetermined rules with the patient information. In various embodiments, the one or more predetermined rule define a causal relationship between an element of the patient information and the failure of compliance. In various embodiments, the one or more predetermined rule is generated by association rule learning.

In various embodiments, retrieving the patient information comprises applying natural language processing to unstructured textual data.

In various embodiments, the one or more potential cause is provided for review on a mobile device.

Figure 4:
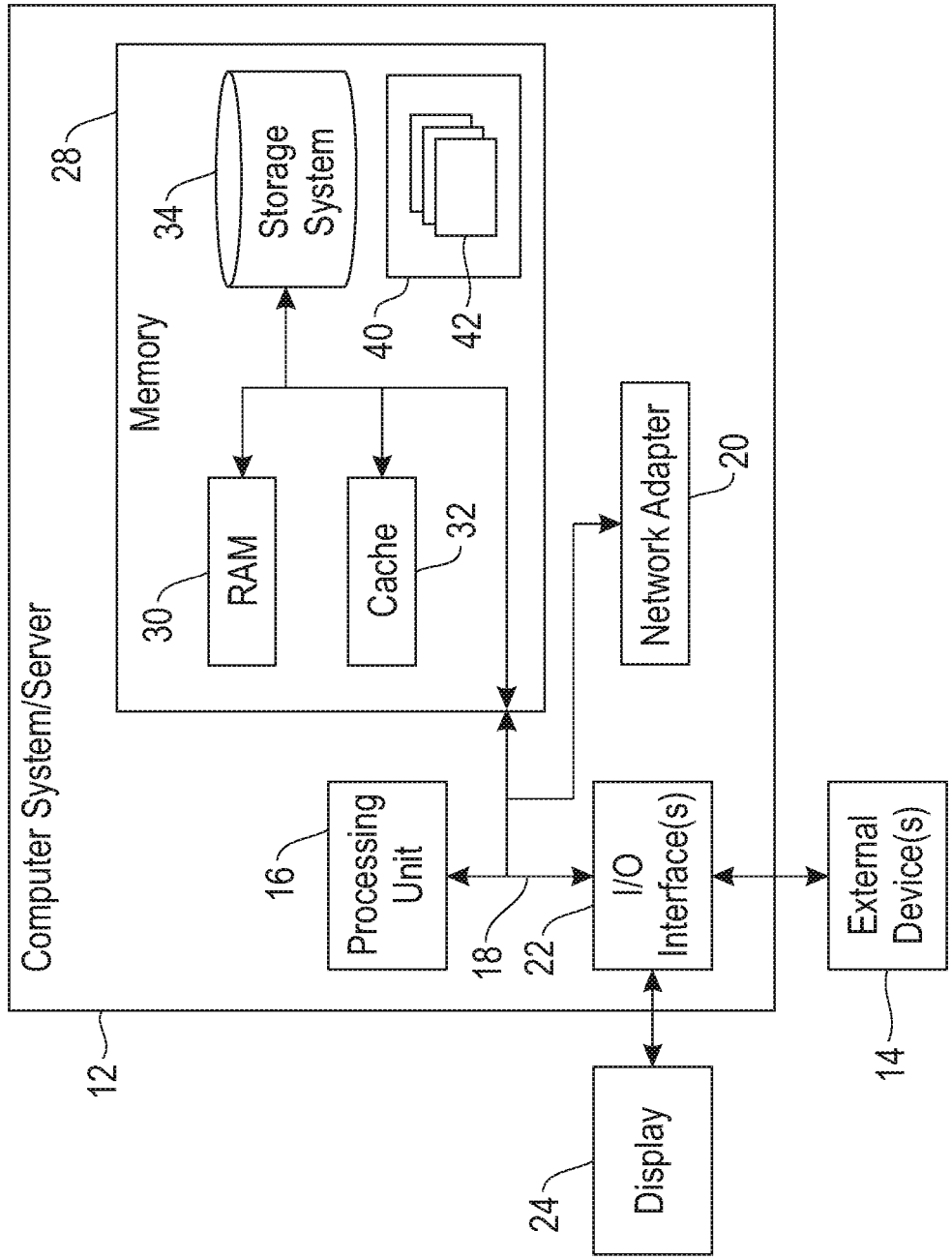
FIG. 4 depicts a computing node according to an embodiment of the present invention.

Referring now to FIG. 4, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
   retrieving, by a processor, patient information for a patient, the patient information comprising a treatment plan;
   determining, by the processor, from the patient information a failure of compliance with the treatment plan by the patient;
   generating one or more predetermined rules by association learning, where each of the one or more predetermined rules define a causal relationship between an element of the patient information and the failure of compliance, wherein association learning comprises applying a rule-based machine learning system to a plurality of causes of failure and a plurality of adherence failures, the failure of compliance being one of the plurality of adherence failures;
   determining, by the processor, one or more potential cause of the failure of compliance by comparing the one or more predetermined rules with the patient information and cross-correlating information from a plurality of sources;
   determining a ranked list of the one or more potential cause of the failure of compliance, the ranked list based on frequency in a general population;
   determining responsible relationships for each of the one or more potential cause of the failure of compliance by analyzing express relationships from social media or by sentiment analysis of messages; and
   providing the ranked list and the responsible relationships to a user for review.

2. The method of claim 1, wherein the patient information further comprises an electronic health record, biometric data, location data, calendar data, or social media data.

3. The method of claim 1, wherein the patient information comprises structured and unstructured data.

4. The method of claim 1, wherein the treatment plan comprises a pharmaceutical dosage regimen.

5. The method of claim 1, wherein determining the failure of compliance comprises comparing one or more treatment event of the patient information with the treatment plan.

6. The method of claim 1, wherein retrieving the patient information comprises applying natural language processing to unstructured textual data.

7. The method of claim 1, wherein the ranked list is provided for review on a mobile device.

8. A system comprising:
   a computing node comprising a computer readable storage medium having program instructions embodied therewith, the program instructions executable by a processor of the computing node to cause the processor to perform a method comprising:
      retrieving patient information for a patient, the patient information comprising a treatment plan;
      determining from the patient information a failure of compliance with the treatment plan by the patient;
      generating one or more predetermined rules by association learning, where each of the one or more predetermined rules define a causal relationship between an element of the patient information and the failure of compliance, wherein association learning comprises applying a rule-based machine learning system to a plurality of causes of failure and a plurality of adherence failures, the failure of compliance being one of the plurality of adherence failures;
      determining one or more potential cause of the failure of compliance by comparing the one or more predetermined rules with the patient information and cross-correlating information from a plurality of sources;
      determining a ranked list of the one or more potential cause of the failure of compliance, the ranked list based on frequency in a general population;
      determining responsible relationships for each of the one or more potential cause of the failure of compliance by analyzing express relationships from social media or by sentiment analysis of messages; and
      providing the ranked list and the responsible relationships to a user for review.

9. A computer program product for determining underlying reasons for lack of treatment adherence, the computer program product comprising a computer readable storage medium having program instructions embodied therewith, the program instructions executable by a processor to cause the processor to perform a method comprising:
   retrieving patient information for a patient, the patient information comprising a treatment plan;
   determining from the patient information a failure of compliance with the treatment plan by the patient;
   generating one or more predetermined rules by association learning, where each of the one or more predetermined rules define a causal relationship between an element of the patient information and the failure of compliance, wherein association learning comprises applying a rule-based machine learning system to a plurality of causes of failure and a plurality of adherence failures, the failure of compliance being one of the plurality of adherence failures;
   determining one or more potential cause of the failure of compliance by comparing the one or more predetermined rules with the patient information and cross-correlating information from a plurality of sources;

determining a ranked list of the one or more potential cause of the failure of compliance, the ranked list based on frequency in a general population;

determining responsible relationships for each of the one or more potential cause of the failure of compliance by analyzing express relationships from social media or by sentiment analysis of messages; and providing the ranked list and the responsible relationships to a user for review.

10. The computer program product of claim 9, wherein the patient information further comprises an electronic health record, biometric data, location data, calendar data, or social media data.

11. The computer program product of claim 9, wherein the patient information comprises structured and unstructured data.

12. The computer program product of claim 9, wherein the treatment plan comprises a pharmaceutical dosage regimen.

13. The computer program product of claim 9, wherein determining the failure of compliance comprises comparing one or more treatment event of the patient information with the treatment plan.

14. The computer program product of claim 9, wherein retrieving the patient information comprises applying natural language processing to unstructured textual data.

15. The computer program product of claim 9, wherein the ranked list is provided for review on a mobile device.

16. The method of claim 1, wherein the plurality of sources comprises at least one of: the patient electronic medical record, pharmacy information, a retail establishment computer system, and a hospital system.

17. The computer program product of claim 9, wherein the plurality of sources comprises at least one of: the patient electronic medical record, pharmacy information, a retail establishment computer system, and a hospital system.

* * * * *